United States Patent
Gomes et al.

(10) Patent No.: US 7,018,659 B2
(45) Date of Patent: Mar. 28, 2006

(54) ANTI-ARRHYTHMIC PHARMACEUTICAL COMPOSITION AND A PROCESS THEREOF

(75) Inventors: Antony Gomes, Kolkata (IN); Archita Saha, Kolkata (IN); Ajoy Kumar Biswas, Kolkata (IN); Subir Chandra Dasgupta, Kolkata (IN)

(73) Assignee: Council of Scientific & Industrial Research, New Delhi (IN)

( * ) Notice: Subject to any disclaimer, the term of this patent is extended or adjusted under 35 U.S.C. 154(b) by 427 days.

(21) Appl. No.: 10/384,768

(22) Filed: Mar. 11, 2003

(65) Prior Publication Data

US 2004/0105893 A1    Jun. 3, 2004

Related U.S. Application Data

(63) Continuation of application No. PCT/IB02/05116, filed on Dec. 2, 2002.

(51) Int. Cl.
*A61K 35/58* (2006.01)

(52) U.S. Cl. ...................................................... 424/542

(58) Field of Classification Search ................. 424/542
See application file for complete search history.

*Primary Examiner*—Jean C. Witz
(74) *Attorney, Agent, or Firm*—Foley & Lardner LLP

(57) ABSTRACT

The present invention relates to an anti arrhythmic pharmaceutical comprising effective amount of compound designated as KCV-CAF obtained from the venom of Indian snake King Cobra *Ophiophagus hannah* and optionally pharmaceutically acceptable ingredients and a process of isolating the said compound KCV-CAF from the venom of the Indian snake King Cobra (*Ophiophagus hannah*).

13 Claims, No Drawings

ANTI-ARRHYTHMIC PHARMACEUTICAL COMPOSITION AND A PROCESS THEREOF

TECHNICAL FIELD

The present invention relates to an anti arrhythmic pharmaceutical comprising of bioactive compound designated as KCV-CAF obtained from the venom of Indian snake King Cobra *Ophiophagus hannah*. The present invention also relates to a process for the isolation of a novel low molecular weight potent anti-arrhythmic agent with potential for pharmacological-therapeutic use from the venom of the Indian snake King Cobra (*Ophiophagus hannah*).

BACKGROUND ART

Cardiovascular diseases, coronary artery disease in particular, are a major cause of mortality worldwide. Genetically determined ethnic propensity of Asian Indians, growing urbanisation, changing lifestyle and increasing level of individual stress not only contributes to premature coronary artery disease but also accelerates the overall incidence of coronary artery disease in the subcontinent. Heart can be considered as a system of muscular mechanical pump with multiple chambers guarded by the valves and coordinated by spreading waves of electrical depolarization down the conduction pathways. Heart's ability to pump depends on its ability to sustain its own metabolic energy deriving procedures which are mostly aerobic and depends critically on coronary circulation; which is jeopardized in case of coronary artery disease and needs urgent revascularization measures including thrombolytic agents. In this setting of abnormal cardiac rhythm (arrhythmia), asynchrony and impaired cardiac contractility leads to heart failure. The left ventricle fails to pump adequately to maintain the tissue perfusion and to meet the metabolic demands of vital organs including brain and kidneys and heart failure ensues. Decreased stroke volume in heart failure leads to reflex rise to heart rate in order to maintain the minute volume which in turn again raises the metabolic demand of the cardiac myocytes further worsening the situation. Failure may progress slowly or can be acute and life threatening. "Sudden Cardiac Death" is a clinical entity with a grave prognosis as death occurs by definition within one hour from the onset of symptoms. (Braunwald E, Mock M B and Watson J. Eds. 1982. Congestive heart failure. Current Research and Clinical Applications. Grune and Stratton).

Medicinal application of the various fractions of snake venom is well known to humankind as depicted in the Ayurveda, Homoeopathy and Unani literatures. Clot resolving effect, anti-tumor effect and analgesic effect of the numerous biomolecules isolated from snake venom has been reported. From the present laboratory, a novel fibrinolytic peptide (Hannahpep) has been isolated from King Cobra venom Patent Application No: 2384/Del/98 dated 13.8.98). However isolation of any anti-arrhythmic or cardiotonic principles from snake venom is not reported till date. However, there is certain other animal venom components, which possess cardiotonic/anti-arrhythmic property. Reference may be made to:

DPI-201-206 (Romey G, Quart U, Pauron D, Frelin C, Renand J and Lazdunski M. 1987. Proc. Natl. Acad. Sci. USA, 84, 896–900) which is a sea-anemone venom toxin which has a positive inotropic combined with a negative chronotropic effect, action potential prolongation and coronary dilating activity.

Cardiopep (Vick J, Shipman W and Brooks R. 1974. Beta adrenergic and anti-arrhythmic effects of cardiopep, a newly isolated substance from whole bee venom. Toxicon, 12, 39–144) a cardioactive anti-arrhythmic substance has been found in bee venom. It has been shown to increase the rate and force of contraction of the heart.

The present invention relates to a process for isolation of an anti-arrhythmic component from King Cobra venom.

The major drawbacks of anti-arrhythmic drugs already in use are that a significant number of available positive inotropic agents have either very narrow margin between their therapeutic and toxic levels or require considerations for adjuvant pharmacological agents in order to antagonize their side effects. Cardiac glycosides for example have very high systemic toxicity and may induce cardiac rhythm abnormalities. Reference may be made to Goodman and Gilman's The Pharmacological basis of therapeutics. $8^{th}$ Edition, 1990. Editors Nies A S, Rall T W, Taylor P, Goodman Gilman A, Pg. 854–857, 861, 863, 870.

The drugs, which improves myocardial contractility without raising the heart rate, free from or have minimal toxicity, and does not interfere with the coagulation but renormalizes the cardiac arrhythmia, would have been an effective agent of choice in treating the cardiac pathophysiological states.

Applicants, for the first time isolated and identified a novel low molecular weight biomolecule from the venom of snake King Cobra, which possesses anti-arrhythmic property. This novel compound had a $\lambda_{max}$ of 225.4 nm, $E_{max}$ of 360 nm when excited at 250 nm and having a molecular weight of 256 Daltons. The novel anti-arrhythmic compound increased the force of contraction and successfully restored the hypodynamic heart and auricle, sparing any change in the heart rate.

OBJECTS OF THE INVENTION

The main object of the invention is to provide an anti-arrhythmic pharmaceutical composition comprising a novel bioactive compound designated as KCV-CAF obtained from the snake venom of the Indian snake King Cobra (*Ophiophagus hannah*).

Another object of the present invention is to provide a process for the isolation of a novel anti-arrhythmic compound useful for pharmacological purposes, from the Indian King Cobra venom.

Another object of the present invention is to provide a process for the isolation of a novel anti-arrhythmic agent useful for therapeutic application in cardiovascular irregularities and as a biomedical research probe/tool.

Yet, another object of the present invention is to provide a process for the isolation of a novel anti-arrhythmic agent from easily available resources such as the snake King Cobra, a natural product of Indian origin.

SUMMARY OF THE INVENTION

Accordingly, the present invention provides a pharmaceutical composition comprising effective amount of a bioactive molecule designated as KCV-CAF from snake venom. The present invention also provides a process for the isolation of a novel anti-arrhythmic biomolecule designated as KCV-CAF, useful for pharmacological purposes.

DETAILED DESCRIPTION OF THE INVENTION

Accordingly, the present invention provides an antiarrythmic compound designated as KCV-CAF obtained from the venom of Indian snake King Cobra *Ophiophagus hannah*.

The said compound is having the following characteristics:
i) molecular weight of the compound is 256 Daltons,
ii) non proteinesious in nature,
iii) Ultraviolet spectra of the compound using methanol as a solvent produces a sharp peak at 225.4 nm,
iv) the said compound produces a sharp peak on RP-HPLC, with a retention time of 7.85 minutes, and
v) on excitation at 250 nm showed an emission maxima ($E_{max}$) at 360 nm, and One embodiment of the invention provides an anti-arrhythmic pharmaceutical composition comprising effective amount of compound designated as KCV-CAF obtained from the venom of Indian snake King Cobra *Ophiophagus hannah*, mixed optionally with one or more pharmaceutically acceptable ingredients.

In an embodiment of the invention, the said compound obtained from the snake venom is having following characteristics: $\lambda_{max}$ 225.4 nm, $E_{max}$ of 360 nm when excited at 250 nm. In another embodiment of the invention, the said bioactive molecule is having a molecular weight of 256 Daltons.

Another embodiment, the pharmaceutically acceptable ingredient is selected from group consisting of nutrients such as proteins, carbohydrates, sugar, talc, magnesium stearate, cellulose, calcium carbonate, starch-gelatin paste and/or carriers, excipient, diluent or solvent.

Still another embodiment, the said composition is administered by way of inhalation, oral, intravenous, intra-muscular, subcutaneous routes or any other suitable routes.

Still another embodiment, the oral route of administration is in the form of capsule, syrup, concentrate, powder or granules.

Yet another embodiment, the amount of composition administered by intravenous route is less than the oral route.

Yet another embodiment, the present invention provides a said composition, revert hypodynamic heart and auricle to normal conditions.

Yet another embodiment, the said composition is non-haemorrhagic and non-hemolytic in nature.

One more embodiment of provides a process for the isolation of a novel anti-arrhythmic biomolecule designated as KCV-CAF useful for pharmacological purposes from snake venom, said process comprising the steps of:
(i) obtaining venom of snake King Cobra;
(ii) purifying the venom of step (i) by repeated known chromatographic methods to obtain the novel anti-arrhythmic compound designated as KCV-CAF.

Another embodiment of the present invention, the venom used is selected from snake King Cobra, such as Indian King Cobra (*Ophiophagus hannah*).

Still another embodiment, the purifying is effected using known chromatographic methods such as thin layer chromatography on silica gel followed by reverse phase high performance liquid chromatography.

Still another embodiment, the novel anti-arrhythmic biomolecule designated as KCV-CAF, is obtained from the snake King Cobra (*Ophiophagus hannah*). The said biomolecule is having a molecular weight 256 Daltons. The said molecule has a maximum ultraviolet absorbance at 225.4 nm, fluorescent property emission maxima ($E_{max}$) of 360 nm when excited at 250 nm.

By the process of the present invention a novel and potent anti-arrhythmic compound has been purified from the venom of the Indian King Cobra (*Ophiophagus hannah*) by thin layer chromatography followed by reverse-phase high performance liquid chromatography. The compound, so obtained, was devoid of haemorrhagic, hemolytic and defibrinogenating activity.

The following examples are given by way of illustration and therefore should not be constructed to limit the scope of the present invention.

EXAMPLE 1

Purification of the Novel Anti-arrhythmic Compound from of Snake Venom

Thin layer chromatography of King Cobra venom was done in pre activated glass plates (20×10 cm) coated with silica gel GF 254, using solvent system isopropanol: 0.1(N) HCl (7:3 v/v). Spots were visualized in (1) UV (254 nm) chamber (2) iodine vapour and $R_f$ value calculated. Rechromatography was done using silica gel G (Type 60) and the same solvent system spots were visualized in (1) iodine vapour (2) 0.1% ninhydrin in acetone and $R_f$ was calculated.

A spot was observed having (1) white fluorescence at 254 nm (2) yellowish brown colour in iodine and whose $R_f$ value was 0.5. Rechromatography of this spot again produced a single spot of $R_f$ 0.5, which appeared pink with ninhydrin. The purification process produced a 0.25±0.02% yield of the active compound.

The TLC purified active compound was passed through millipore filter (0.4μ) and then further purified in reverse phase high performance liquid chromatography (RP-HPLC) Waters 486 system using $C_{18}$ column (60 Å, 4 μm, 3.9×150 mm) using solvent isopropanol (100%).

The active compound produced a single sharp peak on RP-HPLC, with a retention time of 7.85 mins, indicating the active compound to be homogeneous in nature.

Structural/Spectroscopic Analysis and Partial Characterization

The ultraviolet spectra of the compound done in a Shimadzu UV-vis spectrophotometer using spectral methanol as solvent produced a sharp peak at 225.4 nm. The fluorescence spectra of the compound were done in Perkin Elmer MPF 448 fluorescence spectrophotometer using 0.9% saline, pH 7.4 as a solvent. Emission scanned from 260 to 800 nm, when excited at 250 nm showed an emission maxima ($E_{max}$) at 360 nm.

LCMS of the compound showed M+ at m/z 256.

The active compound isolated and purified from the King Cobra venom as mentioned in example 1 was obtained in pure state, non-protein in nature with molecular weight of 256 Daltons.

In the following examples, the biological activities of the novel compound were determined.

EXAMPLE 2

Action on Isolated Auricle

The effect of the novel compound on isolated guineapig auricle was assayed in vitro according to Bum J H (1952).

Practical Pharmacology. Blackwell Scientific Publications, Oxford, 22–25. Oxygenated Ringer's solution was used at temperature of 29±1° C. The compound (2.5 ng/ml) increased the amplitude of contraction by 20±0.2% after (30±5.6) mins observed up to 6 hrs. The auricular rate however remained unchanged.

EXAMPLE 3

Action on Isolated Heart

The effect of this compound on isolated toad heart was assayed in vitro using amphibian Ringer solution at room temperature (28±2° C.) through cannulation of hepatic vein. The compound (20 ng) increased the amplitude of contraction by 18±2% after (15±5.5) mins. The action on isolated guineapig heart was assayed in vitro according to Langendorff, O (1895). Untersuchungen an uberlebenden sangetierheizen. Pfluger Arch ges Physiol. 61, 291–293. Isolated heart was perfused with oxygenated tyrode solution at 37±1° C. The compound (10 ng) increased the amplitude of contraction of isolated guinea pig heart by (12±1.4)% after (20±3.5) mins.

EXAMPLE 4

Action on Hypodynamic Auricle

Isolated guineapig auricle was prepared after Burn J H (1952). Aconitine (15 ng/ml) when added, set up arrhythmia within (40±5) mins. This novel compound (5 ng/ml) could revert arrhythmia to normal within (45±4.2) mins. The normal functioning state was maintained, observed up to 6 hrs. Again, arrhythmia was set in isolated auricle with 2.25 mM $CaCl_2$. Arrhythmia was reverted to normal with the novel compound (5 ng/ml) within (30±3.36) mins of observation.

EXAMPLE 5

Action on Hypodynamic Heart

Isolated toad heart preparation was treated with acotinine (40 ng), to produce arrhythmia. This novel compound (10 ng) could revert, the hypodynamic heart to normal within (24±7.32) mins. Normal heart rate was maintained as observed up to 3±0.5 hrs.

Isolated guineapig heart prepared after Langendorff O. (1895) was made arrhythmic with acotinine (30 ng). On addition of the novel compound (10 ng), arrhythmia was reverted to normal within (42±3.2) mins. Normal heart rate was maintained as observed up to 4±0.5 hrs.

EXAMPLE 6

Electrocardiograph Studies (Normal Heart)

Electrocardiograph studies were conducted on urethane (1.75 g/kg, i.p) anaesthetized male albino Wister rats (150±10 g). Hypodermic needle electrodes were used to record the ECG waves. Recordings obtained with BPL cardiostat instrument in standard lead II (paper speed 25 mm/sec, voltage calibrated at 1 mV). When the novel compound (1 μg/100 g) was infused through the jugular vein, E.C.G. recordings showed the pattern to be the same as before infusion of compound.

EXAMPLE 7

Electrocardiograph Studies (Hypodynamic Heart)

Electrocardiograph studies were conducted on urethane (1.75 g/kg, i.p) anaesthetized male Wister albino rats (150±10 g). Recordings were obtained in lead II. Aconitine (50 μg/100 g) was infused through the jugular vein and arrhythmia was induced within 30±5 mins. The novel compound (1 μg/100 g) was then infused through the jugular vein and started to revert the arrhythmia within 10±5 mins and normalized the hypodynamic heart after 120±10 mins. Repeated administration of the compound (0.5 μg/100 g×3 times) also reverted hypodynamic heart to normal within (90±10) mins.

EXAMPLE 8

Effect on Capillary Permeability

Capillary permeability was tested on mice by blue dye extravasation method (Kellet D N, 1965. On the anti-inflammatory activity of protamine sulphate and of hexadimethrine bromide, inhibitors of plasma kinin formation. Br. J. Pharmac., 24, 703). The novel compound (10 ng)/normal saline for control was injected intradermally to male albino Swiss mice (20 g). After half an hour Evan's Blue (60 mg/kg) was injected intravenously. After 30 mins, the animals were sacrificed and skin removed to measure the diameter of the dye extravasation areas (corresponding to the site of injection) on the inner surface of the skin. This compound did not increase the capillary permeability as compared to the normal.

EXAMPLE 9

Rat Hind Quarter Perfusion Studies

Rat hind quarter perfusion was studied by the method of Burn J H, 1952. Practical Pharmacology, Blackwell Scientific Publications, Oxford, 22–25. In a freshly sacrificed rat, the rectum, inferior and superior mesentric arteries were separated through ligation and after that the intestine was removed. A polyethylene cannula was inserted in the abdominal aorta and the trunk was cut transversely across into two parts above the point of cannulation. The distal portion was laid on a circular piece of gauze attached to a ring, which rested on a polyethylene funnel. Ringer solution at 37±1° C. was perfused through the abdominal aorta at a constant pressure and perfusion was carried out until the perfusate was free of blood. The volume of perfusate per unit time was measured. The novel compound (50 ng) did not produce any change in the perfusate volume per unit time (Control 1.5±0.3 ml/3 mins, expt. 1.5±0.3 ml/3 mins).

EXAMPLE 10

Defibrinogenating Activity

Defibrinogenating activity of the novel anti-arrhythmic compound was assayed in vivo according to Theakston R D G and Reid H A, 1983. Development of simple standard assay procedure for the characterization of snake venom. Bulletine of the World Health Organization, Geneva, Vol. 61, 949–956. The novel compound (1 μg) in 0.9% saline was injected intravenously through the caudal vein in male albino Swiss mice (18–20 g). After 1 hr blood was collected from retro-orbital plexus and defibrinogenating activity was recorded. The blood of the treated animals coagulated within the same time as that of the control animals (0.9% saline injected i.v) i.e. 2±0.2 mins. Thus, the compound did not possess defibrinogenating activity.

EXAMPLE 11

Haemorrhagic Activity

Cutaneous haemorrhagic activity of the novel anti-arrhythmic compound was assayed in vitro in male albino Swiss mice (20 g) after the method of Kondo H, Kondo S, Ikezawa H, Murata R and Ohsaka A, 1969. Studies on the quantitative method of determination of haemorrhagic activity of Habu Snake Venom. Japanese Journal of Medical Science and Biology, Volume 13, 43–51. Minimum haemorrhagic dose (MHD) was defined as the amount to test substance when injected intradermally, produced a haemorrhagic spot of 10 mm diameter within 24 hours of observation. Saline (0.9%) was used as negative control, Russel's viper venom (5 μg) was used as positive control. The novel anti-arrhythmic compound (1 μg) did not produce any haemorrhagic spot observed within 24 hours as compared with positive control (10 mm diameter) Russel's viper venom. Thus, the novel anti-arrhythmic compound was found to be non-haemorrhagic in nature.

EXAMPLE 12

Hemolytic Activity

Hemolytic activity of the novel anti-arrhythmic compound (1 μg) was assayed in vitro by incubating with 1 ml 1% human RBC, guineapig RBC, rat RBC-suspension at 37° C. for 30 min. RBC suspension was centrifuged at 900 g for 30 mins and degree of lysis was measured at 540 nm against negative control (saline 0.9%) and positive control 100% distilled water. The anti-arrhythmic compound did not hemolyse the RBC. Therefore, the novel anti-arrhythmic compound was non-hemolytic in nature.

EXAMPLE 13

The Novel Anti-arrhthmic Compound was Provisionally Designated as KCV-CAF

It may be concluded from the above that a novel anti-arrhythmic compound KCV-CAF has been purified from the venom of the Indian King Cobra (*Ophiophagus hannah*) snake. The compound has a molecular weight of 256 daltons. This novel anti-arrhythmic compound can normalize the functioning of hypodynamic heart and auricle. The novel anti-arrhythmic compound is devoid of haemorrhagic, hemolytic and defibrinogenating activity.

The Main Advantages of the Present Invention are:
(1) The novel anti-arrhythmic compound (KCV-CAF) has been purified from King Cobra Venom, the snake being distributed in India (Sunderbans, north-east hilly regions), Bangladesh, Myanmar, Thailand, Cambodia, Vietnam. (Endoglyphs and other major venomous snakes of the World. A checklist, Golay P, Smith H M, Bloodley D G, Dixon F R, McCarthy C, Page J C, Schatti B, Toriba I M, Azemiops, 1993).
(2) The novel anti-arrhythmic compound (KCV-CAF) has been purified using easy and cheaper conventional methods.
(3) The novel anti-arrhythmic compound (KCV-CAF) can revert the hypodynamic heart and auricle to normal.
(4) The novel anti-arrhythmic compound (KCV-CAF) was non-haemorrhagic and non-hemolytic in nature.
(5) The yield obtained was of the order of 0.25±0.02%.

What is claimed is:

1. An antiarrythmic compound designated as KCV-CAF obtained from the venom of Indian snake King Cobra *Ophiophagus hannah*.

2. The compound as claimed in claim 1 is having the following characteristics:
   i) molecular weight of the compound is 256 Daltons,
   ii) non proteinaceous in nature,
   iii) ultraviolet spectra of the compound using methanol as a solvent produces a sharp peak at 225.4 nm,
   iv) the said compound produces a sharp peak on RP-HPLC, with a retention time of 7.85 minutes, and
   v) on excitation at 250 nm showed an emission maxima ($E_{max}$) at 360 nm.

3. An anti-arrhythmic pharmaceutical composition comprising effective amount of compound designated as KCV-CAF obtained from the venom of Indian snake king cobra *Ophiophagus hannah*, mixed optionally with one or more pharmaceutically acceptable ingredients.

4. The composition as claimed in claim 3, wherein the pharmaceutically acceptable ingredient is selected from a group consisting of proteins, carbohydrates, sugar, talc, magnesium stearate, cellulose, calcium carbonate, starch-gelatin paste and/or carriers, excipient, diluent or solvent.

5. The composition as claimed in claim 3, is administered by way of inhalation, oral, intravenous, intramuscular, subcutaneous routes or any other suitable routes.

6. The composition as claimed in claim 3, wherein the oral route of administration is in the form of capsule, syrup, concentrate, powder or granules.

7. The composition as claimed in claim 3, wherein the amount administered by intravenous route is less than the oral route.

8. The composition as claimed in claim 3, which reverts hypodynamic heart and auricle to normal conditions.

9. The composition as claimed in claim 3, is non-haemorrhagic and non-hemolytic in nature.

10. Process for the isolation of a anti-arrhythmic compound designated as KCV-CAF useful for pharmacological purposes, said process comprising steps of:
    i. obtaining venom of snake king cobra; and
    ii. purifying the venom of step (a) by repeated chromatographic methods to obtain the novel anti-arrhythmic compound KCV-CAF.

11. A process as claimed in claim 10, wherein the venom used is that of snake such as Indian king cobra (*Ophiophagus hannah*).

12. A process as claimed in claim 10, wherein the purifying is effected using chromatographic methods thin layer chromatography on silica gel followed by reverse phase high performance liquid chromatography (HPLC).

13. A process as claimed in claim 10, wherein the anti-arrhythmic compound designated as KCV-CAF obtained from the snake king cobra (*Ophiophagus hannah*) venom has a molecular weight 256 Daltons, maximum ultraviolet absorbance at 225.4 nm, fluorescent properties emission maxima ($E_{max}$) of 360 nm when excited at 250 nm.

* * * * *